US008298272B2

(12) United States Patent
Edie et al.

(10) Patent No.: US 8,298,272 B2
(45) Date of Patent: Oct. 30, 2012

(54) SELF-LOCKING SURGICAL FASTENER

(75) Inventors: Jason A Edie, Salt Lake City, UT (US); Matthew David Schultz, Memphis, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 1023 days.

(21) Appl. No.: 12/189,935

(22) Filed: Aug. 12, 2008

(65) Prior Publication Data

US 2010/0042162 A1 Feb. 18, 2010

(51) Int. Cl.
*A61B 17/86* (2006.01)
(52) U.S. Cl. ........................................................ 606/301
(58) Field of Classification Search .......... 606/300–305, 606/319; 411/21, 80.1–80.6, 396, 508, 913
See application file for complete search history.

(56) References Cited

U.S. PATENT DOCUMENTS

| | | | |
|---|---|---|---|
| 4,636,121 A | 1/1987 | Miller | |
| 4,952,106 A * | 8/1990 | Kubogochi et al. | ............. 411/48 |
| 5,478,342 A | 12/1995 | Kohrs | |
| 5,849,004 A | 12/1998 | Bramlet | |
| 5,984,927 A | 11/1999 | Wenstrom, Jr. et al. | |
| 6,447,546 B1 | 9/2002 | Bramlet et al. | |
| 6,471,707 B1 * | 10/2002 | Miller et al. | ................... 606/916 |
| 6,695,844 B2 | 2/2004 | Bramlet et al. | |
| 6,752,576 B2 * | 6/2004 | Johansson et al. | .............. 411/21 |
| 2002/0045898 A1 | 4/2002 | Freid et al. | |
| 2002/0156473 A1 | 10/2002 | Bramlet et al. | |
| 2006/0276789 A1 | 12/2006 | Jackson | |
| 2008/0097444 A1 | 4/2008 | Erickson et al. | |

FOREIGN PATENT DOCUMENTS

| | | |
|---|---|---|
| DE | 10101267 A1 | 12/2001 |
| DE | 29805443 U1 | 12/2001 |
| FR | 2856272 A | 12/2004 |

OTHER PUBLICATIONS

International Search Report, Jul. 31, 2009.

* cited by examiner

*Primary Examiner* — Nicholas Woodall

(57) ABSTRACT

The present application is directed to self-locking surgical fasteners. The fastener generally includes a shaft section, a head section, and one or more locking members. The locking members may be located within the head section. A first portion of the locking members may extend beyond an outer surface of the head section, and a second portion of the locking members may extend into a hollow interior of the head section. A tool used to insert the fastener into the patient engages a receiver portion of the fastener. As the insertion tool engages the receiver, the tool may contact and exert a force on the locking member such that the first portion of the locking member may be retracted within the head section. Upon disengaging the insertion tool from the receiver, the locking member may return to the position extending outward beyond the outer surface of the head section.

9 Claims, 9 Drawing Sheets

SELF-LOCKING SURGICAL FASTENER

BACKGROUND

The present application is directed to surgical fasteners and, more particularly, to surgical fasteners that are self-locking once positioned within the patient and that allow for removal of the fastener after positioning.

Surgical fasteners, such as screws, pins, rivets, hooks, and the like, are often used for securing an implant within a patient. The implant is positioned within a patient's body and the surgical fasteners are inserted through apertures in the implant and into a bone (or other substrate) to fixedly connect the implant. Surgical fasteners may also be used independently to secure sections of a broken bone to one another.

One type of surgical procedure that utilizes surgical fasteners is the attachment of an implant, such as a vertebral plate, to vertebral members. The vertebral plate is sized to extend across two or more of the vertebral members such that the vertebral plate either limits movement of or provides additional support to the vertebral members. One or more surgical fasteners extend through apertures in the plate and into the vertebral members to secure the plate. One issue with this procedure is that the surgical fasteners may loosen and back out of the vertebral members over time. Correction usually requires another surgical procedure to either re-tighten the surgical fasteners to the bone, or removal and replacement of the fasteners and/or plate. Surgical fastener locking devices may be necessary to prevent the fastener from backing out of the support member.

SUMMARY

The present application is directed to self-locking surgical fasteners. The fastener generally includes a shaft section, a head section, and one or more locking members. The locking member may be located within the head section. A first portion of the locking member may extend beyond an outer surface of the head section, and a second portion of the locking member may extend into a hollow interior of the head section. A tool used to insert the fastener engages a receiver of the fastener. As the insertion tool engages the receiver, the tool may contact and exert a force on the locking member such that the first portion of the locking member may be retracted within the head section. Upon disengaging the insertion tool from the receiver, the locking member may return to the position extending outward beyond the outer surface of the head section.

DETAILED DESCRIPTION

The present application is directed to surgical fasteners that are self-locking when inserted, for example, into a bone or an implant. The fastener may include a body and one or more locking members. The body may further include a receiver sized to receive a tool for insertion and removal of the fastener. The body further includes a proximal section which may have a generally hollow interior. A first portion of the locking member may extend beyond an outer surface of the body. A second portion of the locking member may also extend beyond an outer surface of the body or may extend into the hollow interior. In use, the tool engages the receiver and contacts the second portion of the locking member. This contact exerts a force on the locking member causing the locking member to move, and the first portion of the locking member retracts inward within the head section. When the tool is disengaged from the receiver, the first portion of the locking member may return to a position extending beyond the outer surface of the body.

Figure 1:
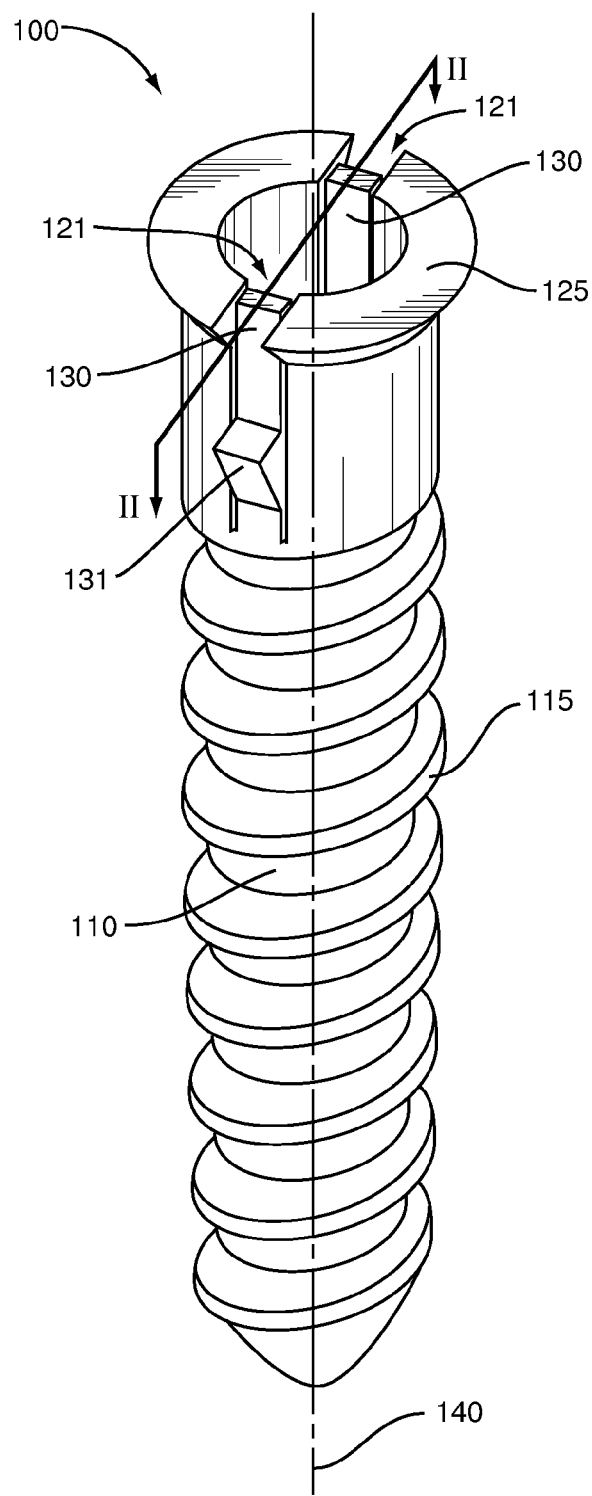
FIG. 1 is a perspective view illustrating a self-locking surgical fastener according to one embodiment.

FIG. 1 illustrates one embodiment of a fastener, indicated generally as 100. The fastener 100 includes a shaft section 110, a head section 120, and one or more locking members 130. Fastener 100 is constructed for insertion into a patient. In one embodiment, fastener 100 is used to attach an implant or like device within the patient. In another embodiment, fastener 100 is used independently, such as to connect together sections of a fractured vertebral member.

The shaft section 110 is typically formed as an elongated body that extends along an axis 140. Threads 115 may extend along a portion or entirety of the shaft section 110. A distal end of the shaft section 110 may terminate at a pointed tip to facilitate insertion into the patient. In one embodiment, a receiver 200 (FIG. 2) may be positioned at a proximal end of the shaft section 110. The receiver 200 is configured to engage with a tool 300 (FIG. 3) to drive the fastener 100 into the patient. The receiver 200 may include a variety of shapes and sizes to receive various types of tools 300, including but not limited to a Phillips screwdriver, a flathead or straight screwdriver, a Torx® driver, and an Allen wrench.

The head section 120 is joined to the proximal end of the shaft section 110. The head section 120 may be formed integrally with the shaft section 110, or may be a separate component attached to the shaft section 110 by a threaded connection, interference fit, adhesive, mechanical fastener, or the like. The head section 120 may be generally cylindrical in shape and aligned axially with the shaft section 110 along axis

140. A flange 155 (FIG. 2) may extend around the periphery of the head section 120. The head section 120 may include a generally hollow interior 215 (FIG. 2) to allow access to the receiver 200. The head section 120 may include slots 121 to allow movement of the locking members 130.

Figure 2:
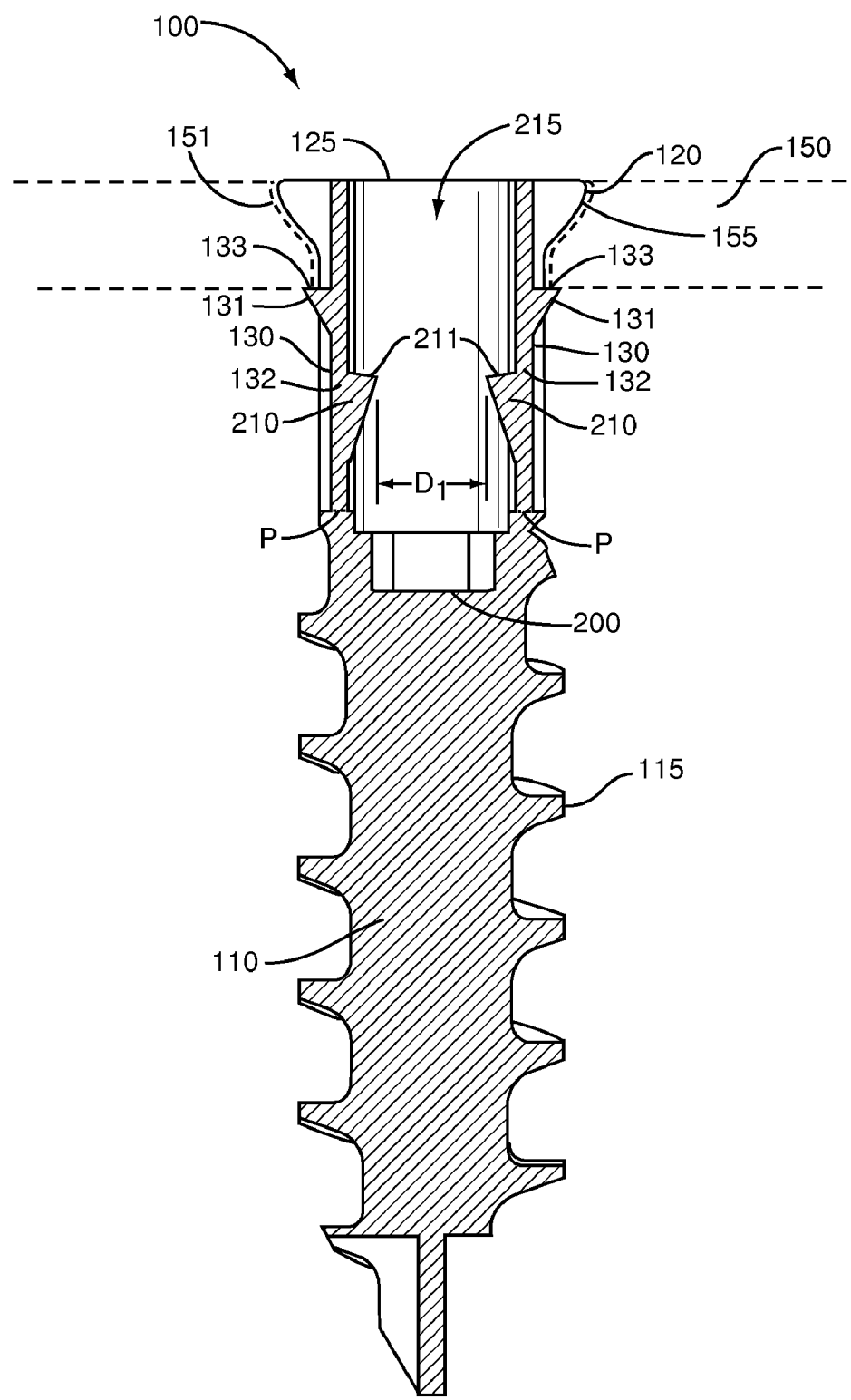
FIG. 2 is a sectional view illustrating a self-locking surgical fastener according to one embodiment.
Figure 9:
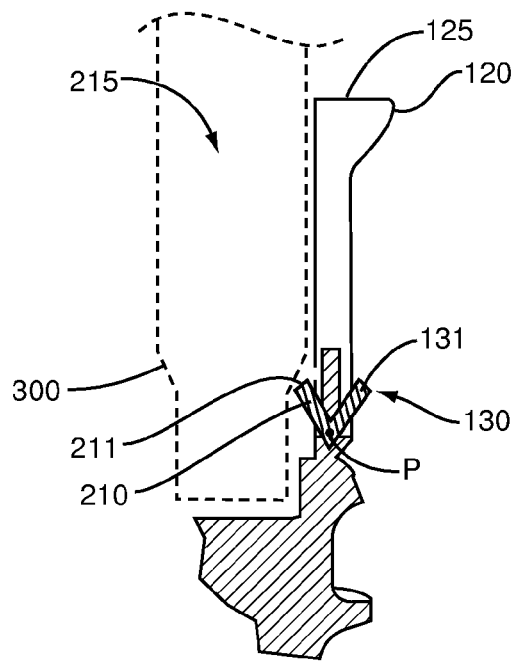
FIG. 9 is a partial sectional view illustrating a locking member according to one embodiment.

Locking members 130 are positioned to prevent back-out of the fastener 100. FIGS. 1 and 2 illustrate one embodiment of locking members 130. Each locking member 130 includes an elongated arm 132. The arm 132 may include an exterior contact member 131 and an interior contact member 210. The exterior contact member 131 faces outward away from the axis 140, and the interior contact member 210 faces inward towards the axis 140. In this embodiment, the exterior contact member 131 and the interior contact member 210 are also vertically offset from one another such that the exterior contact member 131 is positioned closer to a top surface 125 of the fastener 100 than the interior contact member 210. This orientation facilitates a pivoting movement of the locking member 130 as discussed in more detail below. Other orientations of the exterior contact member 131 and the interior contact member 210 relative to one another are also possible, such as transversely oriented as shown in FIG. 9.

Figure 3:
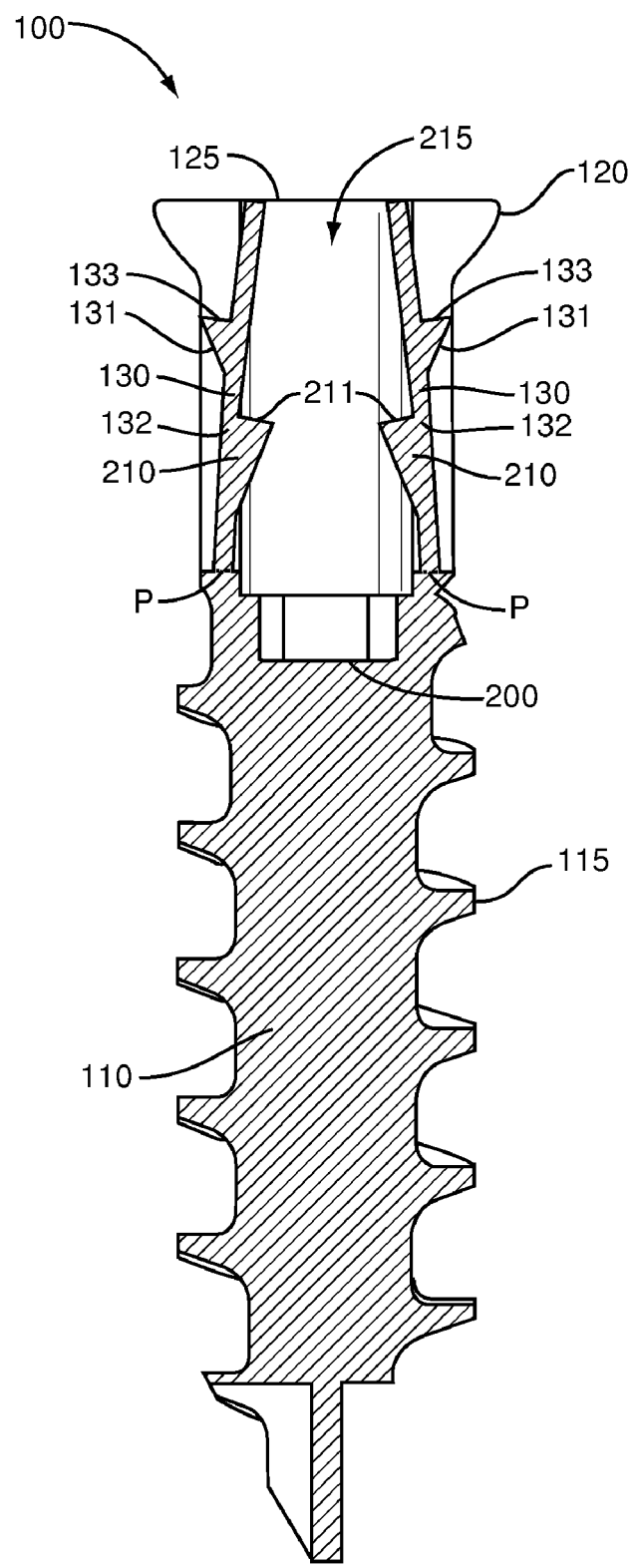
FIG. 3 is a sectional schematic view illustrating a self-locking surgical fastener according to one embodiment.

The locking members 130 are generally positioned in a first orientation as illustrated in FIGS. 1 and 2 with the exterior contact member 131 extending outward from the head section 120 to prevent back-out of the fastener 100. In one embodiment, the interior contact member 210 is positioned within the hollow interior 215. During insertion of the tool 300 into the hollow interior 215, the interior contact member 210 is contacted causing the exterior contact member 131 to pivot inward towards the hollow interior 215 to a retracted, second orientation as illustrated in FIG. 3. The second, retracted orientation allows insertion and removal of the fastener 100 from the patient.

The embodiment illustrated in FIGS. 1 and 2 include slots 121 in the head section 120 to allow the pivoting movement of the locking members 130. In this embodiment, the locking members 130 are typically integrally formed with the head section 120 or the shaft section 110. Alternately, the locking members 130 may be a separate component that is inserted into the hollow interior 215 of the head section 120.

In one embodiment, the exterior contact member 131 includes a top surface 133. After the fastener 100 is inserted into the patient, an entirety or a section of the exterior contact member 131 extends beyond the outer surface of the head section 120. The top surface 133 contacts the implant or bone to prevent back-out of the fastener 100. FIG. 2 illustrates the fastener 100 inserted through a hole 151 in an implant 150. The exterior contact member 131 of locking mechanism 130 extends beyond the outer surface of the head section 120 and extends beyond an edge of the hole 151. The top surface 133 of the exterior contact member 131 contacts the implant 150 and prevents the fastener 100 from backing out.

In the retracted, second orientation, the locking member 130 moves inward forming a width less than a width of the hole 151 to allow for insertion and removal of the fastener 100. FIG. 3 illustrates one embodiment of the fastener 100 with the locking members 130 in the retracted, second orientation. As shown, the locking members 130 are retracted such that the entire exterior contact member 131 is within the outer surface of the head section 120. Further retraction of the locking members 130 beyond the outer surface of the head section 120 is not required, but may be achieved so long as the elastic limit of the locking member 130 is not exceeded.

The top surface 133 is shown as a flat surface in FIGS. 1 and 2. The top surface 133 may also include other shapes such as concave and convex, and may also include texturing to further aid in preventing movement of the fastener 100 once inserted within the patient. Further, the top surface 133 may be positioned at a variety of angles relative to the axis 140 when the locking member 130 is in the first orientation.

Figure 4A:
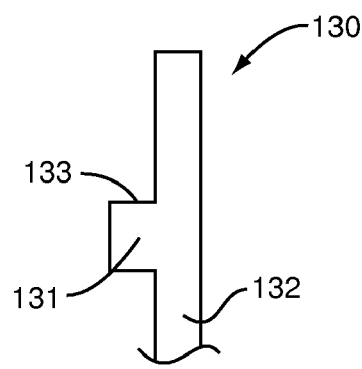
FIG. 4A is a partial schematic view illustrating a locking member according to one embodiment.
Figure 4B:
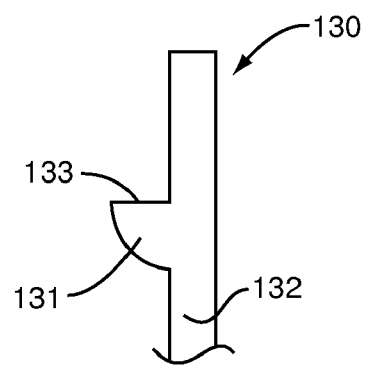
FIG. 4B is a partial schematic view illustrating a locking member according to one embodiment.
Figure 4C:
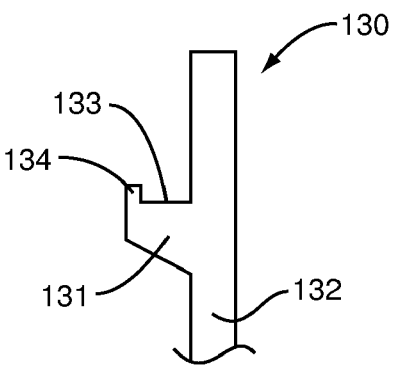
FIG. 4C is a partial schematic view illustrating a locking member according to one embodiment.

As shown in FIGS. 1 and 2, the exterior contact member 131 is a generally triangular shaped protrusion, which functions to efficiently transfer forces imposed on the top surface 133 to the arm 132. Other shapes are also contemplated, such as a rectangular shape as illustrated in the embodiment of FIG. 4A and a semicircular shape as illustrated in the embodiment of FIG. 4B. FIG. 4C further illustrates an embodiment with the exterior contact member 131 including a lip 134 extending upward beyond the top surface 133. The lip 134 may engage a slot or hole in an implant in which the fastener 100 is inserted to further prevent movement of the fastener 100. The lip 134 may also penetrate the substrate in which the fastener 100 is inserted (for example, when the fastener 100 is used to secure sections of a broken bone together) to secure the fastener 100 from further movement.

Figure 5:
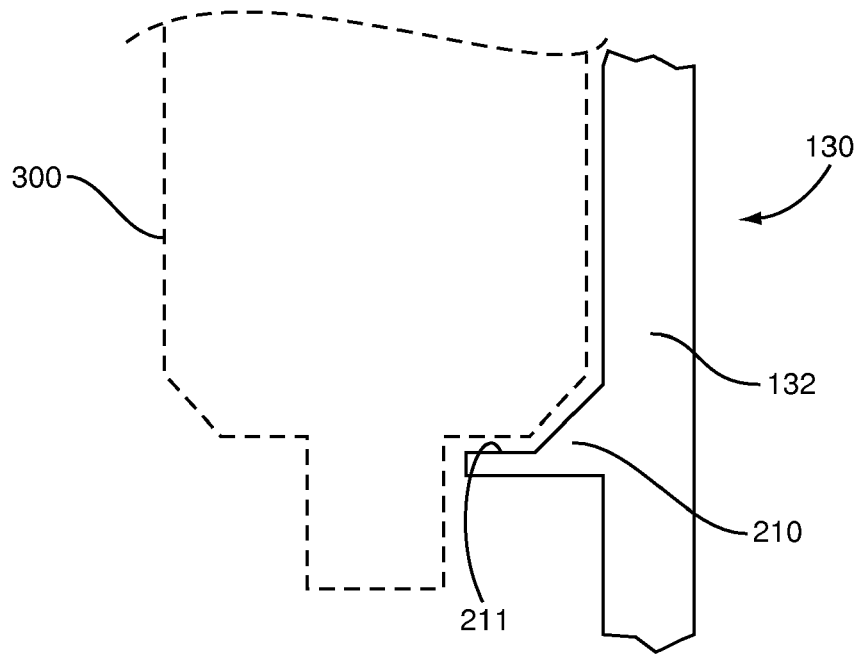
FIG. 5 is a partial schematic view illustrating a locking member according to one embodiment.

The interior contact member 210 as shown in the embodiment of FIGS. 1 and 2 is generally a triangular shaped protrusion, one side of which forms a contact surface 211 for contacting a tool 300 during insertion into the receiver 200. The contact surface 211 in this embodiment is generally perpendicular to the axis 140. This orientation facilitates the transfer of a downward force on the contact surface 211 when the tool 300 makes contact with the contact surface 211. In addition, the orientation allows the contact surface 211 to remain in contact with the tool 300 as the locking member 130 pivots in response to the downward force. As described previously for the exterior contact member 131, the interior contact member 210 may have a variety of shapes such as but not limited to triangular, rectangular, and semicircular. In another embodiment illustrated in FIG. 5, the contact surface 211 may be oriented to accommodate a particular shape of the tool 300.

Figure 6A:
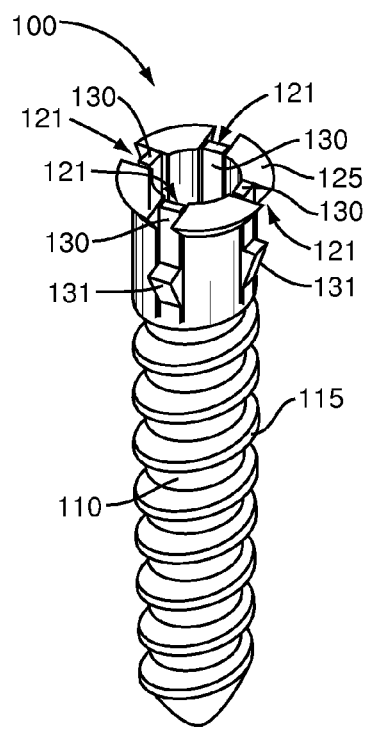
FIG. 6A is a perspective view illustrating a self-locking surgical fastener according to one embodiment.
Figure 6B:
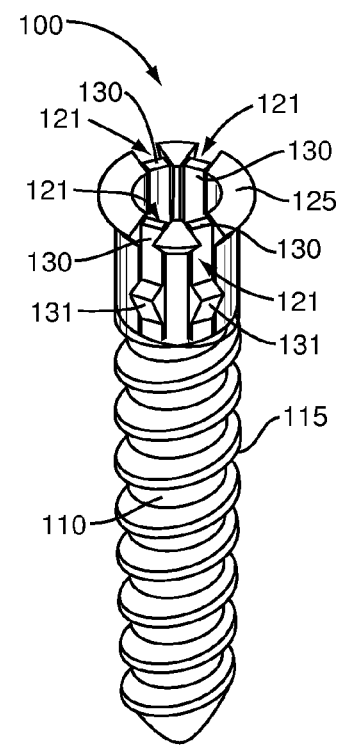
FIG. 6B is a perspective view illustrating a self-locking surgical fastener according to one embodiment.
Figure 6C:
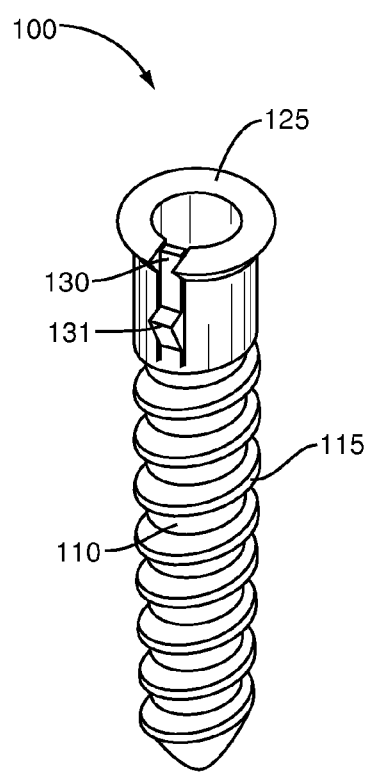
FIG. 6C is a perspective view illustrating a self-locking surgical fastener according to one embodiment.

The embodiment illustrated in FIGS. 1 and 2 includes two locking members 130 disposed 180 degrees opposite one another in the head section 120. Other numbers of locking members 130 and other orientations of the locking members 130 within the head section 120 are also contemplated as may be required for a particular application. FIG. 6A illustrates an embodiment with four locking members 130 disposed evenly apart by about 90 degrees from one another within the head section 120. FIG. 6B illustrates an embodiment with four locking members 130 disposed unequally within the head section. FIG. 6C illustrates an embodiment with a single locking member 130.

Figure 7:
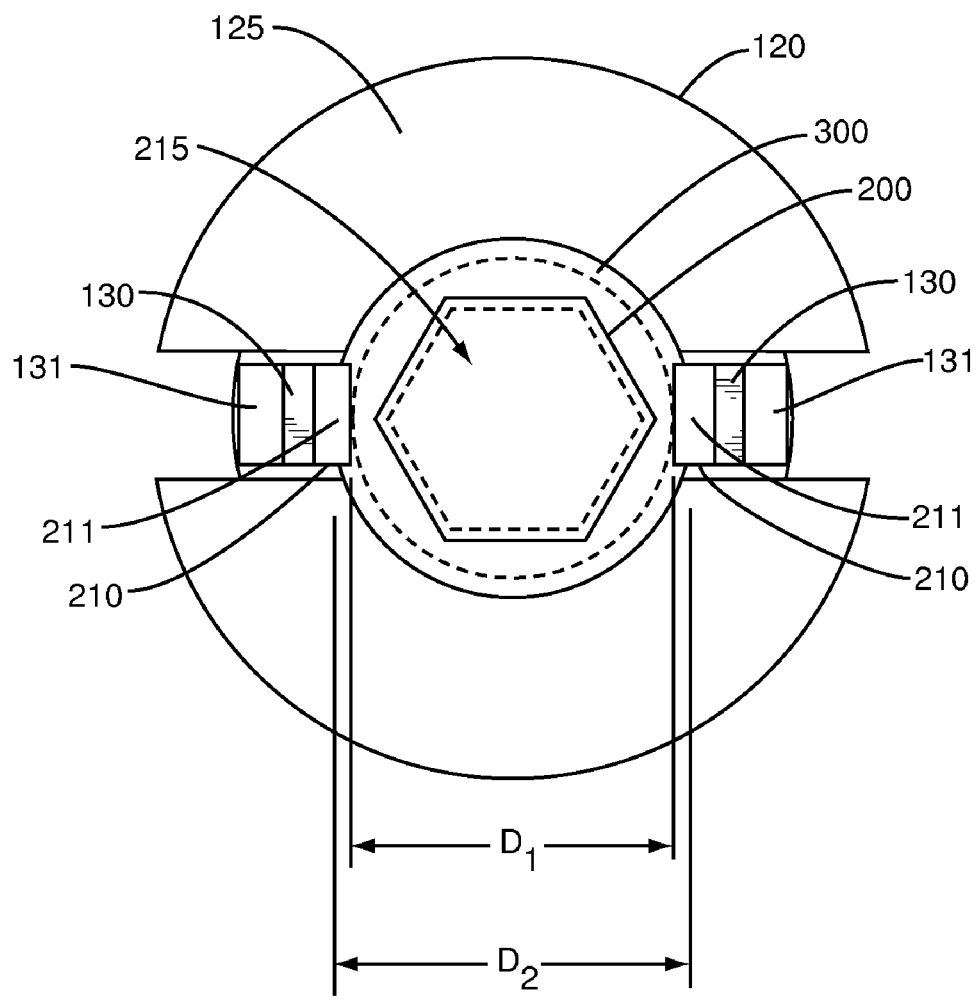
FIG. 7 is a top schematic view illustrating a tool inserted within a self-locking surgical fastener according to one embodiment.

FIG. 7 illustrates a top view of an embodiment of the fastener 100. The tool 300 is shown by the dashed lines and has a hexagonal-shaped drive to engage a similarly shaped receiver 200. The tool 300 and the receiver 200 may assume other shapes as discussed previously. The tool 300 has an outer diameter $D_2$ which is greater than the distance $D_1$ between the contact surfaces 211 of the interior contact members 210. As described more fully below, in one embodiment the tool 300 is inserted into the hollow interior 215 of the head section 120, and contacts the contact surfaces 211. The locking members 130 are caused to pivot inward, and the exterior contact members 131 may retract within the outer surface of the head section 120.

Figure 8:
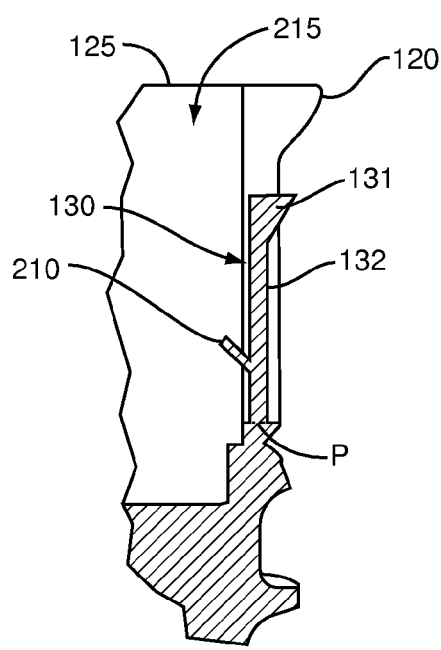
FIG. 8 is a partial sectional view illustrating a locking member according to one embodiment.

FIG. 8 illustrates a detail of one embodiment of the locking member 130. In this embodiment, the interior contact member 210 is configured as a post extending angularly upward from the arm 132 into the hollow interior 215 of the head section 120. The cross-sectional shape of the interior contact member 210 may be round, oval, rectangular, or other suitable configuration. The interior contact member 210 may be positioned lower within the head section 120 than the exterior contact member 131 to facilitate a pivoting movement of the locking member 130. The interior contact member 210 may engage a corresponding hole or slot in the tool 300 as the tool 300 is inserted into the hollow interior 215. As the tool 300 moves downward, the interior contact member 210 is drawn further into the hole or slot. The locking member 130 may be pulled inward by this action and may pivot about point P, retracting the exterior contact member 131 within the head section 120.

FIG. 9 illustrates a detail of one embodiment of the locking member 130. The locking member 130 is a separate piece attached to the head section 120. In this embodiment, locking member 130 includes a substantially V-shape with the interior contact member 210 and the exterior contact member 311 located at about the same position relative to a top surface 125 of the head section 120. The contact surface 211 may be oriented to accommodate the exterior surface of the tool 300, and may also have a textured surface to increase the frictional contact between the tool 300 and the contact surface 211. The exterior contact member 311 may be shaped according to the configurations discussed above for the embodiment of FIGS. 1 and 2.

In this embodiment of FIG. 9, the tool 300 contacts the contact surface 211 of the interior contact member 210 during insertion of the tool 300 into the hollow interior 215 of the head section 120. The tool 300 may impart a downward force on the interior contact member 210, causing the locking member 130 to pivot about point P (i.e., in a counter-clockwise direction as viewed in FIG. 9). The exterior contact member 131 may then be retracted within the head section 120.

Figure 10:
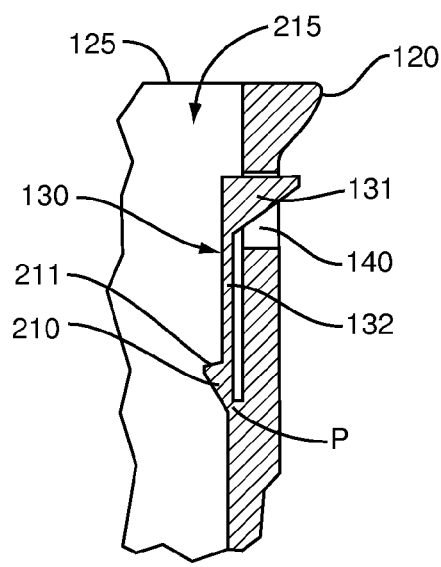
FIG. 10 is a partial sectional view illustrating a locking member according to one embodiment.

FIG. 10 illustrates a detail of one embodiment of the locking member 130. In this embodiment, the arm 132 is located primarily within the hollow interior 215 of the head section 120 as compared to within a slot 121 as illustrated in FIG. 1. An opening 140 is provided to allow the exterior contact member 131 to extend beyond the exterior surface of the head section 120. The contact surface 211 is oriented to accommodate the exterior surface of the tool 300, and may also have a textured surface to increase the frictional contact between the tool 300 and the contact surface 211. The exterior contact member 311 may be shaped according to the configurations discussed above for the embodiment of FIGS. 1 and 2. In this embodiment, the tool 300 engages the contact surface 211 of the interior contact member 210 and may exert a downward force on the locking mechanism 130. The locking member 130 may pivot about point P, causing the exterior contact member 131 to retract within the head section 120.

Figure 11:
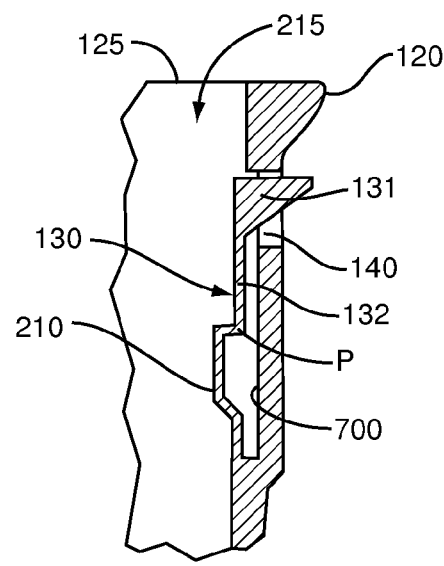
FIG. 11 is a partial sectional view illustrating a locking member according to one embodiment.

FIG. 11 illustrates a detail of another embodiment in which the locking member 130 is located primarily within the hollow interior 215 of the head section 120. In this embodiment, the interior contact member 210 comprises a bend in the arm 132 of the locking member 130 that extends into the hollow interior 215. The bend may comprise a three-sided protrusion as shown in FIG. 11. In other embodiments, the bend may be two-sided, or may have a circular shape. Bends with greater than three sides are also contemplated. The interior contact member 210 may have a textured surface to increase the frictional contact with the tool 300. The exterior contact member 311 may be shaped according to the configurations discussed above for the embodiment of FIGS. 1 and 2. The tool 300 contacts the bend and compresses the bend against an interior wall 700 of the head section 120. This compressive force may cause the locking member 130 to pivot about point P which retracts the exterior contact member 131 within the head section 120.

The locking member 130 to be a separate component that is inserted into the hollow interior 215. The fastener 100 may then be used with or without the self-locking feature, as required for a particular application.

The operation of the locking mechanism is described as follows. Referring to FIG. 2, the interior contact members 210 are situated such that a distance $D_1$ between the interior contact members is less than a width of the tool 300. As the tool 300 is inserted into the hollow interior 215 of the head section 120, the tool 300 contacts the contact surface 211 of one or more interior contact members 210. This contact exerts a force on the locking members 130 that causes the locking members 130 to pivot inwardly about point P. As the tool 300 is inserted further into the hollow interior 215, the locking members 130 may continue to pivot until the exterior contact members 131 are retracted within the head section 120.

The tool 300 may then engage the receiver 200, and the fastener 100 may be driven by the tool 300. The receiver 200 may be positioned lower in relation to the head section 120 than the interior contact members 210 so that the tool 300 contacts the interior contact members 210 before the tool 300 engages the receiver 200. After movement of the fastener 100 is completed, the tool 300 is removed from the hollow interior 215 of the head section 120. The locking member 130 may be biased such that the locking member 130 assumes a position which extends the exterior contact member 131 beyond the outer surface of the head section 120 when not acted upon by forces resulting from inserting the tool 300 into the hollow interior 215 of the head section 120. In one embodiment, the fastener 100 is inserted through an implant and into a bone. The exterior contact members 131 extend underneath the implant and prevent the fastener from backing out or unscrewing.

Figure 12:
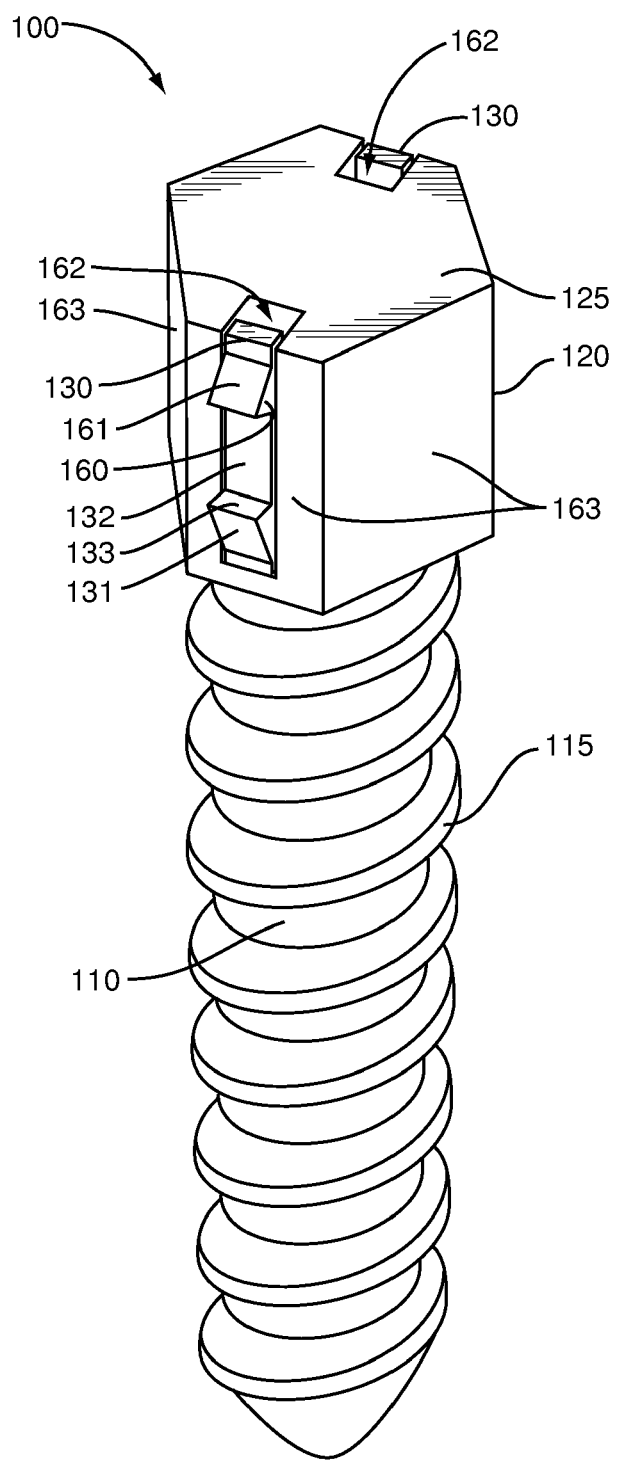
FIG. 12 is a perspective view illustrating a self-locking surgical fastener according to one embodiment.
Figure 13:
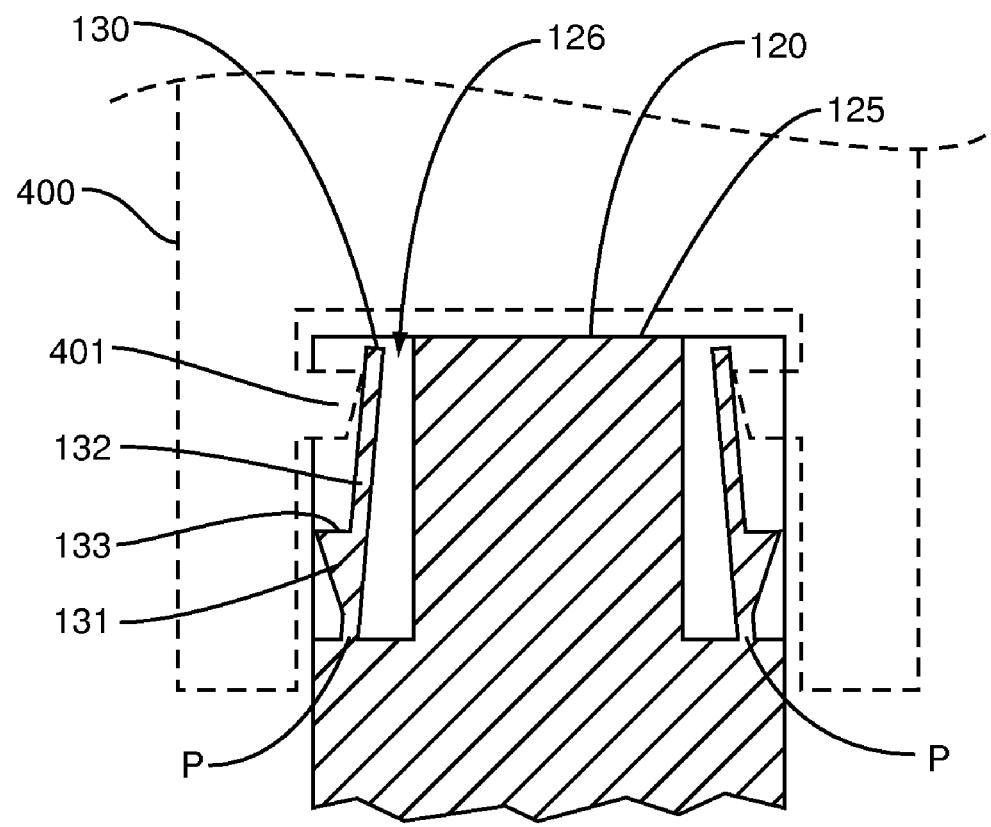
FIG. 13 is a sectional view illustrating a self-locking surgical fastener according to one embodiment.

In some embodiments as described above, the receiver 200 is positioned within the fastener 100. In another embodiment, the receiver 200 is positioned on an exterior of the fastener 100. FIGS. 12 and 13 illustrate embodiments with the head section 120 including a number of generally flat exterior receiver surfaces 163. In these embodiments, a tool 400 (FIG. 13) engages one or more of the receiver surfaces 163 to drive the fastener 100 into the patient. The contact with the tool 400 moves the locking members 130 into a second orientation.

In the embodiment of FIG. 12, the locking members 130 include an elongated arm 132. The arm 132 includes an exterior contact member 131 having a top surface 133. The arm 132 may further include an exterior tool engaging member 160 having a top surface 161. The exterior contact member 131 and the exterior tool engaging member 160 each extend outward from the arm 132. In this embodiment, the exterior contact member 131 and the exterior tool engaging member 160 are vertically offset from one another such that the exterior tool engaging member 160 is positioned closer to a top surface 125 of the fastener 100 than the exterior contact member 131. When the tool 400 is inserted over the head section 120, the tool engaging member 160 is contacted causing the arm 132 to pivot inward to a second orientation. Once the tool 400 is removed, the arm pivots outward and returns to the first orientation.

In the embodiment of FIG. 13, the arm 132 includes only the exterior contact member 131. The locking member 130 is moved to the second, retracted position by making contact with a protrusion 401 on an inner surface of the tool 400. In this embodiment, the protrusion 401 is aligned with a slot 162 in the head section 120, and then the tool 400 is engaged with the head section 120. The protrusion 401 contacts the arm 132 and causes the locking member 130 to pivot about point P to the second retracted orientation.

The embodiments illustrated in FIGS. 12 and 13 include slots 162 in the head section 120 to allow the pivoting movement of the locking members 130. In this embodiment, the locking members are typically integrally formed with the head section 120 or a shaft section 110. Alternately, the locking members 130 may be a separate component attached to the head section 120 of the shaft section 110. The embodiment illustrated in FIG. 12 includes a head section 120 with six receiver surfaces 163. Embodiments with a greater or lesser number of receiver surfaces 163 are also contemplated.

The fastener 100 may be made of a variety of materials, including but not limited to titanium, stainless steel, cobalt chrome, other metals, plastics, bio-absorbable material, or a combination thereof. The shaft section 110, head section 120, and locking mechanism 130 may comprise unitary members, or may have a multi-piece construction. The shaft section 110 may be self-tapping or self-threading. The contact surface 211 of the interior contact member 210 may have a roughened or uneven surface to increase frictional contact with the tool 300.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical fastener comprising:
   an elongated body with a distal end and a proximal end, the proximal end including a hollow interior;
   a receiver socket located within the hollow interior; and
   a locking mechanism operatively connected to the body and positioned between the proximal end and the receiver socket, the locking mechanism including a first section and a second section, the first section movable between a first position such that the first section extends outward beyond an outer surface of the body and a second position such that the first section is recessed into the body when the second section is contacted by a tool.

2. The fastener of claim 1 wherein the locking mechanism second section further comprises a contact surface that extends into the hollow interior, the contact surface being positioned at a non-parallel orientation relative to an axis of the elongated body.

3. The fastener of claim 1, wherein the locking mechanism second section is positioned within the proximal end and includes a contact surface that extends into the hollow interior.

4. The fastener of claim 3, wherein the contact surface is located farther away from the proximal end of the body than the locking mechanism first section.

5. The fastener of claim 1, wherein the locking mechanism is configured to connect to the body to pivot when a force is applied to the contact surface.

6. The fastener of claim 1, wherein the first section and second section of the locking mechanism form an elongated arm with the first section connected to the body.

7. The fastener of claim 1, wherein the locking mechanism is integrally formed with the body.

8. The fastener of claim 1, further comprising a second locking mechanism operatively connected to the body, the second locking mechanism being spaced away from the locking mechanism.

9. The fastener of claim 1, wherein the receiver socket is located farther away from the proximal end of the body than the locking mechanism.

* * * * *